Figure 1:
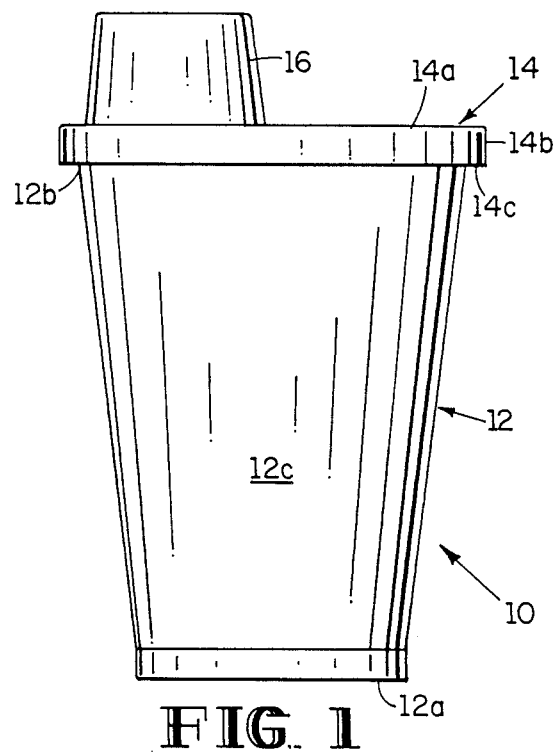
Figure 2:
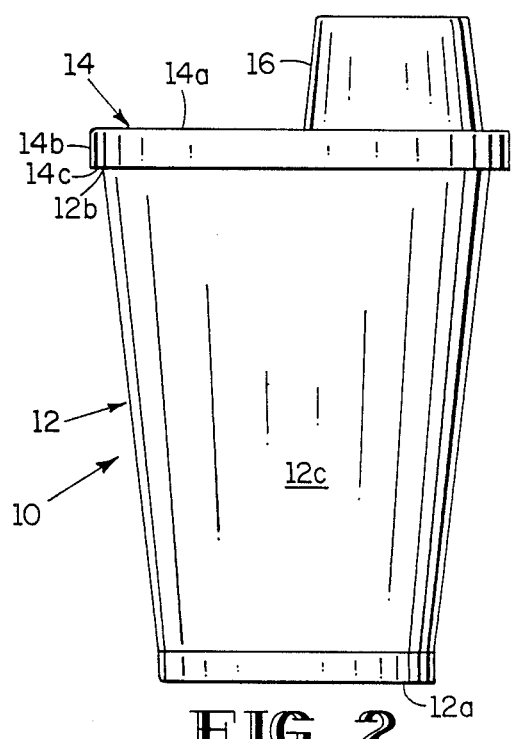
Figure 3:
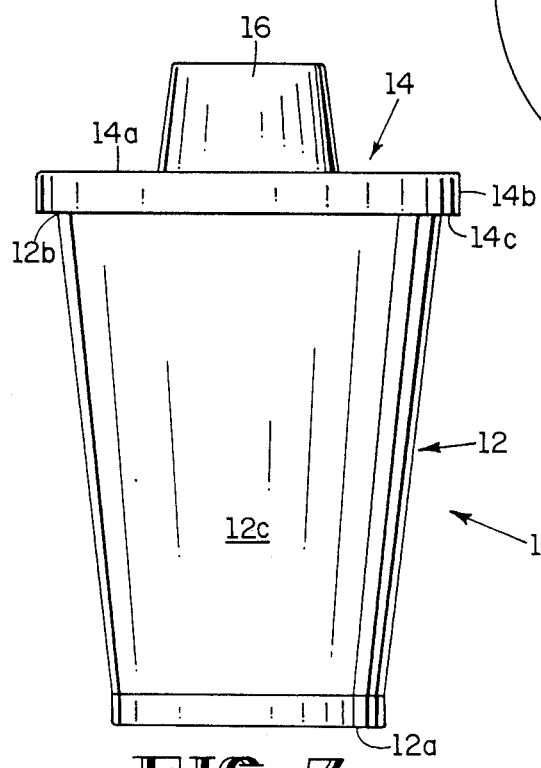
Figure 4:
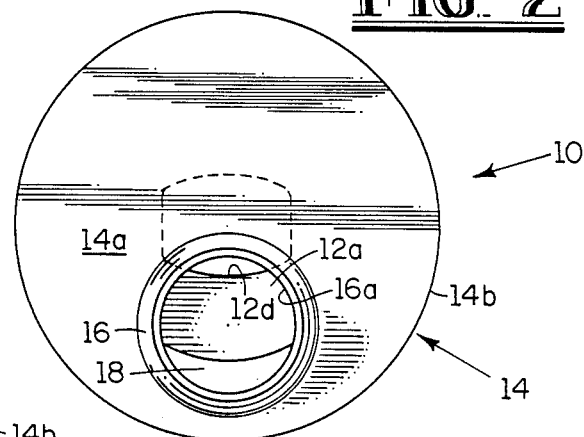
Figure 5:
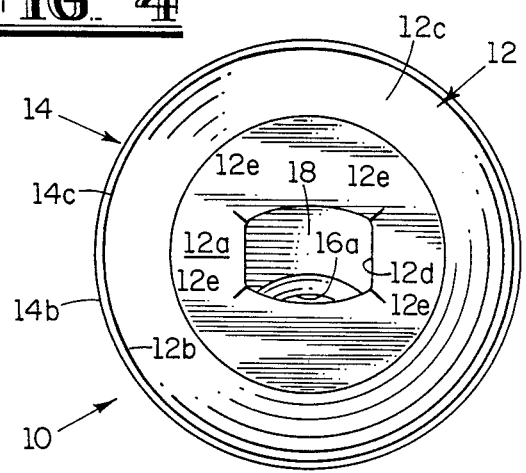
Figure 6:
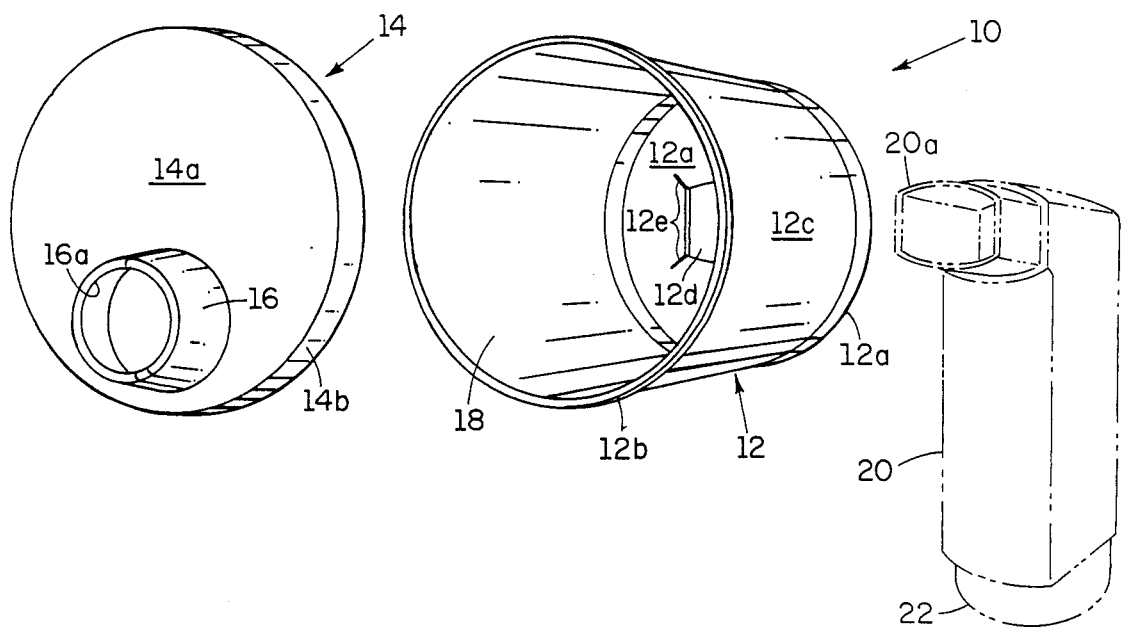
Figure 7:
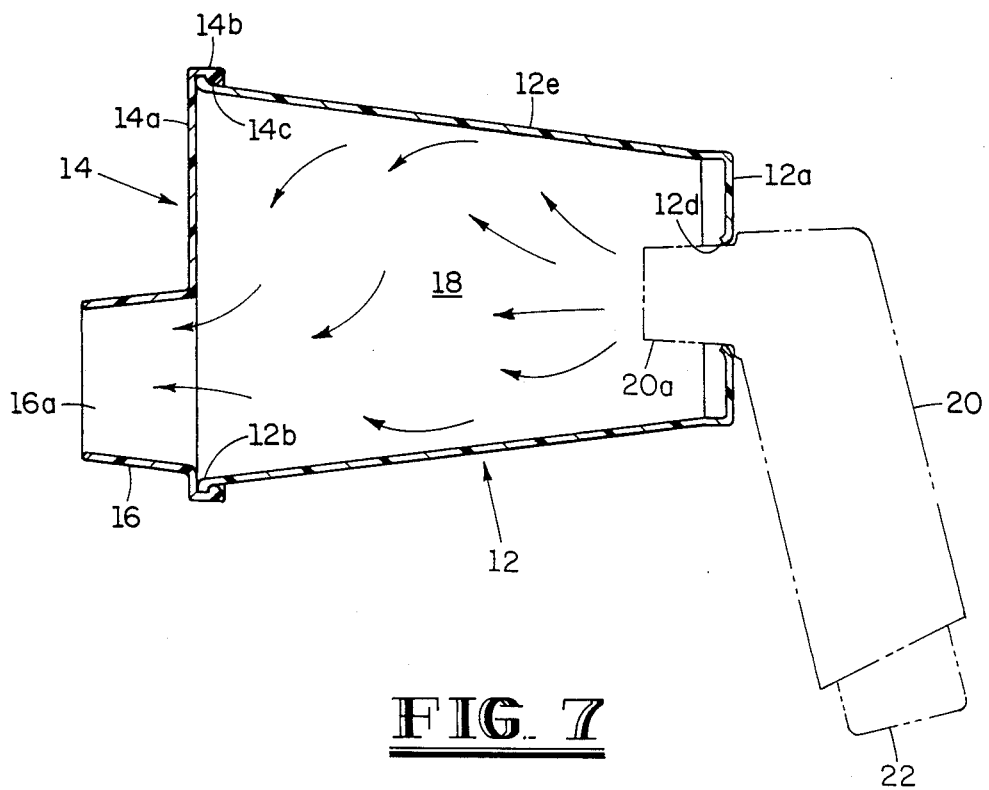

United States Patent [19]

McCarty

[11] Patent Number: 4,953,545
[45] Date of Patent: Sep. 4, 1990

[54] DISPOSABLE RESPIRATORY MEDICATION DISPERSION CHAMBER

[76] Inventor: Jerry McCarty, 8305 Windway Dr., San Antonio, Tex. 78239

[21] Appl. No.: 423,352

[22] Filed: Oct. 18, 1989

[51] Int. Cl.$^5$ ............................................. A61M 11/00
[52] U.S. Cl. ............................ 128/200.23; 128/200.14
[58] Field of Search ....................... 128/200.14, 200.23

[56] References Cited

U.S. PATENT DOCUMENTS

| 3,774,602 | 11/1973 | Edwards | 128/200.16 |
| 4,174,712 | 11/1979 | Morèz et al. | 128/200.14 |
| 4,534,343 | 8/1985 | Nowacki et al. | 128/200.23 |
| 4,637,528 | 1/1987 | Wachinski et al. | 128/200.23 |
| 4,641,644 | 2/1987 | Anderson et al. | 128/200.23 |
| 4,706,663 | 11/1987 | Makiej | 128/200.23 |

FOREIGN PATENT DOCUMENTS

| 0265163 | 4/1988 | European Pat. Off. | 128/205.12 |
| 2110543 | 6/1983 | United Kingdom | 128/200.23 |

Primary Examiner—Edgar S. Burr
Assistant Examiner—Kimberly L. Asher

[57] ABSTRACT

A disposable, independent hand-held chamber for the purpose of dispersing aerosol respiratory medication delivered from metered-dose inhalers that comprises an elongated, tapered chamber with an aperture on smaller end for insertion of metered-dose inhaler and mouthpiece on larger end for inhalation of released aerosol medication.

1 Claim, 2 Drawing Sheets

U.S. Patent  Sep. 4, 1990  Sheet 1 of 2  4,953,545

DISPOSABLE RESPIRATORY MEDICATION DISPERSION CHAMBER

BACKGROUND—FIELD OF INVENTION

This invention relates to disposable respiratory medication dispersion chambers, specifically for placement between metered-dose inhalers and user's mouth.

BACKGROUND—DESCRIPTION OF PRIOR ART

There are some 40,000,000 persons in the United States suffering from various respiratory disease problems varying in severity from person to person. The three main diseases are asthma, emphysema and bronchitis. Asthma and bronchitis are predominant and are reversible to some extent. Inhaled medications provide the most dramatic relief from symptoms of asthma and bronchitis. Various brands of hand-held inhaler-dispensers of medication are available. They release medication from a pressurized canister which causes medication to be sprayed into user's mouth for inhalation.

The problem with most of these hand-held dispensers, usually referred to as metered-dose inhalers, is that they spray a high velocity and narrowly concentrated stream of medication. A large part of the medication deposits on the moist surfaces of user's mouth, teeth and oropharynx. This diminishes the amount of medication available for inhalation. User's coordination of release of medication and inhalation presents a problem for users, particularly for children and the elderly.

Prior art has developed several devices to attempt to overcome the shortcomings of the metered-dose inhalers. Some representatives of the prior art are 4,706,663 Makiej, 4,641,644 Anderson et al, 4,470,412 Nowacki et al, and 4,637,528 Rorer et al.

One of the most important features any device that is placed between a metered-dose inhaler and a user's mouth must possess is cleanliness of said device. All non-disposable devices must be cleaned daily by the user to prevent bacterial contamination and to remove accumulated medication residue from the inside surfaces from which medication is inhaled. All above named prior art requires daily cleaning. The average user as well as the elderly and children are not technically qualified to know if they adequately clean their device. Bacteria are invisible to the naked eye and most of the medication is hard to see as well. Moreover, the inside of the cylinders or chambers of the above named devices are not visible for adequate inspection. The above named devices have one or more screens, valves, diaphragms or other velocity impeding parts. Medication and bacteria are more difficult to remove from these parts. One device named above, 4,470,412 Nowacki et al, directs user to clean device with alcohol. This is not only costly but accidental inhalation of any residue of alcohol fumes or droplets could cause problems for users.

Because these respiratory diseases cause inflamation in the respiratory tract, users must be very careful to avoid bacterial and viral infections. Such infections cause victims of respiratory diseases to have severe breathing problems. Drastic medical intervention may be required to treat these infections. Clean inhalation devices are a necessity to help avoid these infections.

OBJECTS AND SUMMARY OF THE INVENTION

This invention relates to independent disposable hand-held devices for the dispersion of inhalable respiratory medication dispensed under pressure from independent hand-held inhaler-dispensers, usually referred to as metered-dose inhalers.

Various pharmaceutical manufacturers market a variety of metered-dose inhalers dispensing inhalable medication for users to relieve symptoms of various respiratory diseases such as, but not limited to, asthma, emphysema, and bronchitis. These devices are hereinafter referred to as metered-dose inhalers.

These metered-dose inhalers consist of a pressurized canister containing medication to be inhaled. The canisters are incorporated into an adapter with a receptacle portion to hold the canister and a mouthpiece portion for user to place in or near mouth for inhalation of released pressureized medication. Medication is released by user pressing down on one end of the canister causing a valve on the opposite end to release a single dose of the medication through the mouthpiece. User must closely coordinate the release and inhalation or medication will be lost.

In most cases, dispensing the medication under pressure in this manner results in a narrow, high velocity stream of medication. This causes a substantial amount of the medication to be lost. Loss is caused by the deposit of the medication on the lips and moist surfaces of the mouth, teeth and oropharynx of user. These deposits can often lead to irritation of the oropharynx. Loss of medication in this manner can result in under-medication. This slows relief of symptoms. Loss can also result in more frequent inhalations to be needed. This increases the opportunity for irritation of the oropharynx and increased cost for the user.

Many users of these metered-dose inhalers find it difficult to coordinate inhalation with the release of medication. This is a particularly troublesome aspect when children and the eldery try to use these metered-dose inhalers. More often than not, they make several releases of medication before they can coordinate inhalation with release of medication. Again, this causes under-medication, increase opportunity for irritation of the oropharynx and increased cost because of the ineffective releases.

There are devices on the market to insert between the metered-dose inhalers and the user's mouth. These devices are non-disposable and require user to thoroughly clean them each day. Cleaning is required to remove accumulated medication deposits and bacterial contamination. Many users lack the expertise or even the physical ability to thoroughy clean these devices correctly. This is particularly true in the case of children and the elderly. A problem with these devices is that the inside of the chamber of these devices is inaccessible for cleaning and proper inspection. These devices incorporate a variety of screens and valves that are difficult to clean properly.

The present invention is a disposable dispersion chamber to be used between the metered-dose inhaler and the user's mouth. It is cup-shaped with universal accomodating aperture on the small end and a mouthpiece on the large end. Made of thin plastic material, the cost will be just pennies a day and no cleaning will be required because it is disposable.

The foremost object of this invention is to provide users with a clean, disposable dispersion chamber that will permit users of metered-dose inhalers to release the medication into a clean chamber and disperse medication for users to slowly inhale without the necessity to coordinate inhalation with release. The chamber is large enough to allow large particles or droplets of medication to precipitate and become unavailable for inhalation.

Another object of this invention is to provide a clean and bacteria-free chamber for user's use each day at a cost of just pennies a day.

Another object of this invention is to provide hospitals with a germ-free disposable dispersion chamber that will permit more than one patient to be treated by the same metered-dose inhaler.

Another object of this invention is to provide physicians with a germ-free disposable dispersion chamber that will permit many patients undergoing pulmonary function tests to be medicated by the same metered-dose inhaler.

Another object of this invention is to make it easier for users to inhale the maximum available medication without loss of medication by deposits in the mouth and oropharynx.

Another object of this invention is to simplify the inhalation from metered-dose inhalers by the uncoordinated, particularly children being medicated by adults and elderly users by permitting user to release and inhale medication without coordinating the two acts.

Still further, it is a object of this invention to decrease the cost of medication to the user by eliminating wasted releases and by making maximum medication available for relief of symptoms.

THE DRAWINGS

Details and advantages of this invention will be described and pointed out in connection with the attached drawings showing the invention in actual size which:

FIG. 1 is a perspective view of the dispersion chamber.

FIG. 2 is the opposite of FIG. 1, perspective view of the dispersion chamber.

FIG. 3 is a top or bottom horizontal view of the dispersion chamber.

FIG. 4 is a perspective view of the large or mouthpiece end of the dispersion chamber.

FIG. 5 is a perspective view of the small or insertion end of the dispersion chamber.

FIG. 6 is an exploded view of the dispersion chamber and a representative of various brands of metered-dose inhalers.

FIG. 7 is a perspective view of the dispersion chamber with a representative of various brands of metered-dose inhalers inserted into the small or insertion end of the dispersion chamber.

REFERENCE NUMERALS IN DRAWINGS

12 Wall of chamber
**12*a*** Small or insertion end of chamber
**12*b*** Large or mouthpiece cap end
**12*c*** Inside wall
**12*d*** Aperture in small end
**12*e*** Cuts in corners of aperture
14 Cap or mouthpiece-large-end of chamber
**14*a*** Top of cap
**14*b*** Rim of cap
**14*c*** Inside of rim
16 Mouthpiece of chamber
18 Inside of chamber
20 Adapter for metered-dose inhaler
**20*a*** Mouthpiece of adapter
22 Pressurized medication canister

DETAILED DISCLOSURE OF ILLUSTRATIVE EMBODIMENT

First reference is to FIG. 6, **20*a*, 20 and 22 for an understanding of the method of operation of a representative metered-dose inhaler as marketed by various pharmaceutical firms. Pressurized canister of medication 22 inserts into adapter 20. User places mouthpiece 20*a* in or near user's mouth. User must then press down sharply on exposed end of canister 22 and simultaneously inhale through mouthpiece 20*a* the medication released by the downward pressure on canister 22**.

Medication from metered-dose inhaler is released in the form of a concentrated, high velocity stream. FIG. 7 illustrates interior view of the invention with a representative metered-dose inhaler inserted into the universally acceptable aperture **12*d*. The arrows in FIG. 7, 18 illustrate how the released medication is allowed to swirl inside the dispersion chamber toward the mouthpiece 16**. This allows large particles or droplets in the released medication to precipitate and avoid being inhaled.

After the medication is released the user may then inhale the dispersed medication from the said chamber through mouthpiece 16 without the necessity of coordinating inhalation with release from canister 22. It is inevitable that with each release small amounts of medication deposit on inside wall **12*c* of this or any other similar type chamber. However, more medication is available for inhalation from the chamber 18 than from direct inhalation by use of adaptor 20. This is because chamber 18 slows velocity and disperses medication for inhalation reducing deposits on moist surfaces of user's mouth and oropharynx. Since this invention is disposable, user need not attempt to clean accumulated medication residue and bacteria build-up from chamber 18**.

The entire unit is cup-shaped for the purpose of accomodating the narrow, high velocity stream of medication and allows medication to disperse and pecipitate large particles or droplets. This also permits the unit, FIG. 1, FIG. 2 and FIG. 3 to "nest" when packaged to save space for users and retailers. Mouthpiece 16 on cap end FIG. 6, 14 is also designed to "nest" so that cap 14 for large end of chamber will also "nest" in packaging. Smaller end **12*a* of the chamber is an integral, inseparable part of chamber 12. FIG. 5 illustrates the aperture 12*d* for the insertion of mouthpiece 20*a* of adapter 20 of a metered-dose inhaler. The semi-oval shape of the aperture 12*d* accomodates most adapter 20*a* mouthpieces. Aperture 12*d* is also cut at the corners 12*e* to allow flexibility in the plastic so that aperture 12*d*** will also accomodate mouthpieces of other shapes and sizes.

Simplicity of design and manufacture of this invention will make available to individual users as well as hospitals and physicians, a clean and economical dispersion chamber. Users of metered-dose inhalers will be able to enhance treatment as well as reduce their costs.

The preceding description of the invention is an illustration that does not place any limitations of this invention. Various changes and modifications such as, but not limited to, size, shape or material of construction may be made so long as the relevant features of the invention remain the same.

I claim the following for this invention:

1. A disposable medication dispersion device for use with commercially available metered-dosage inhalers, comprising an elongated, tapered chamber having a second cross-section;

said chamber being constructed of plastic material;

said chamber having a flat, small end;

an insertion aperture located centrally in said small end;

said aperture having a substantially oval shape with four corners;

said aperture further having a cut at each of said corners;

said cuts permitting said aperture to accomodate various sizes and shapes of commercially available metered-dosage inhalers;

said chamber further having a large open end having an exterior edge;

said open end being covered by a removable cap;

said cap having a round, tapered mouthpiece being significantly off-set from the center of the cap;

said cap having a rim that forms a bead-like member that engages the exterior edge of the large open end of said dispersion chamber;

said chamber having a longitudinal axis that runs through the center of said small end, said cap, and said chamber;

said insertion aperture being significantly off-set relative to said longitudinal axis.

* * * * *